US011331501B2

(12) United States Patent
Armesto et al.

(10) Patent No.: US 11,331,501 B2
(45) Date of Patent: May 17, 2022

(54) IMPLANTABLE PULSE GENERATOR WITH MULTIPLE SUTURE PORTS

(71) Applicants: Greatbatch Ltd., Clarence, NY (US); Galvani Bioelectronics Limited, Middlesex (GB)

(72) Inventors: Ignacio A. Armesto, Montevideo (UY); Luis Daniel Villamil, Montevideo (UY); Refet Firat Yazicioglu, Stevenage (GB); Kristina Schlegel, Stevenage (GB); Kent Leyde, Collegeville, PA (US)

(73) Assignees: Greatbatch Ltd., Clarence, NY (US); Galvani Bioelectronics Limited, Middlesex (GB)

( * ) Notice: Subject to any disclaimer, the term of this patent is extended or adjusted under 35 U.S.C. 154(b) by 95 days.

(21) Appl. No.: 16/446,681

(22) Filed: Jun. 20, 2019

(65) Prior Publication Data
US 2019/0388696 A1  Dec. 26, 2019

Related U.S. Application Data

(60) Provisional application No. 62/688,415, filed on Jun. 22, 2018.

(51) Int. Cl.
*A61N 1/37* (2006.01)
*A61N 1/375* (2006.01)
*A61N 1/05* (2006.01)

(52) U.S. Cl.
CPC ....... *A61N 1/37518* (2017.08); *A61N 1/3758* (2013.01); *A61N 1/37512* (2017.08);
(Continued)

(58) Field of Classification Search
CPC ............ A61N 1/37518; A61N 1/37512; A61N 1/3758; A61N 1/37514; A61N 1/0534;
(Continued)

(56) References Cited

U.S. PATENT DOCUMENTS 5,871,514 A    2/1999  Wiklund et al.
6,609,029 B1 *  8/2003  Mann .................. A61N 1/3752
                                                              607/37
(Continued)

FOREIGN PATENT DOCUMENTS

CN         108096706 A        6/2018
EP           3381390 A1 * 10/2018 ............... A61F 2/40
WO    WO-2006096686 A1 *  9/2006 ............. A61B 6/032

OTHER PUBLICATIONS

St Jude Medical Proclaim™ IPG Clincan's Manual; 2015; p. 6-p. 7 and Figure 4 (Year: 2015).*
(Continued)

Primary Examiner — Shirley X Jian
(74) Attorney, Agent, or Firm — Michael F. Scalise

(57) ABSTRACT

A device that is implantable in body tissue of a human or animal. The device is comprised of a header comprising at least one terminal adapted for removable connection to a lead and an open ended case closed by a plate to form a housing. The housing is comprised of a surrounding edge wall joined to a first side wall and a second side wall opposed to the first side wall. At least a first suture port extends through the edge wall and the second side wall but not the first side wall at an upper edge region of the housing. A second suture port may extend through the surrounding edge wall and the second side wall but not the first side wall in a similar manner. A third suture port may extend through the header. The three suture ports may define a triangular attachment configuration.

21 Claims, 11 Drawing Sheets

(52) U.S. Cl.
CPC .......... *A61N 1/0534* (2013.01); *A61N 1/0539* (2013.01); *A61N 1/0558* (2013.01); *A61N 1/37514* (2017.08)

(58) Field of Classification Search
CPC .. A61N 1/0539; A61N 1/0558; A61N 1/3752; A61N 1/057; A61N 1/375; A61N 1/362; A61N 1/3968; A61N 1/0543; A61N 1/36046; A61N 1/3754; A61N 1/0563; A61N 1/36125; A61N 1/3622; A61N 1/372; A61N 1/37205; A61N 1/37211; A61N 1/37229; A61N 1/3787; A61N 1/3918; A61N 1/3956; A61N 1/3981; A61N 1/3605; A61N 1/39; A61F 2/14; B65H 2220/09; B65H 2301/33214; B65H 2301/33312; B65H 2403/481; B65H 2404/14; B65H 2513/104; B65H 2513/41; B65H 2801/06; B65H 85/00; B65H 2220/01; B65H 2220/02; B65H 2220/08; B65H 2220/11; A61B 17/0401; A61B 5/0002; A61B 5/0031; A61B 5/02028; A61B 5/02055; A61B 5/021; A61B 5/0215; A61B 5/026; A61B 5/0295; A61B 5/031; A61B 5/036; A61B 5/0464; A61B 5/0535; A61B 5/6837; A61B 17/1325; A61 17/1327; A61B 5/6882; B29C 45/0001; B29C 45/14467; H01R 13/73; H01R 2201/12; Y10T 29/4922; Y10T 29/49925; A61M 15/0086; A61M 2205/43; A61M 2205/59
See application file for complete search history.

(56) References Cited

U.S. PATENT DOCUMENTS

| | | | |
|---|---|---|---|
| 7,383,085 B2 | 6/2008 | Olson | |
| 7,653,434 B1* | 1/2010 | Turcott | A61B 5/0031 607/5 |
| 7,761,165 B1* | 7/2010 | He | A61N 1/0551 607/36 |
| 8,849,420 B2* | 9/2014 | Kane | H01R 43/00 607/116 |
| 2002/0138114 A1 | 9/2002 | Gramse | |
| 2004/0073122 A1 | 4/2004 | Stofer et al. | |
| 2004/0215280 A1 | 10/2004 | Dublin et al. | |
| 2005/0267381 A1 | 12/2005 | Benditt et al. | |
| 2006/0184204 A1* | 8/2006 | He | A61N 1/378 607/2 |
| 2007/0179581 A1 | 8/2007 | Dennis et al. | |
| 2009/0171420 A1* | 7/2009 | Brown | A61N 1/3787 607/60 |
| 2012/0221074 A1 | 8/2012 | Funderburk et al. | |
| 2013/0116763 A1* | 5/2013 | Parker | A61N 1/3787 607/117 |
| 2014/0228905 A1* | 8/2014 | Bolea | A61F 5/56 607/42 |
| 2015/0018877 A1* | 1/2015 | Nolan | B29C 45/14467 606/232 |
| 2015/0196218 A1* | 7/2015 | Wahlstrand | A61N 1/37518 600/378 |
| 2015/0290465 A1* | 10/2015 | Mashiach | H02J 50/12 607/61 |
| 2017/0050030 A1 | 2/2017 | Gottsche et al. | |
| 2018/0028824 A1* | 2/2018 | Pivonka | A61N 1/36062 |
| 2018/0185661 A1* | 7/2018 | Imran | A61M 31/002 |
| 2018/0272122 A1* | 9/2018 | Rys | A61N 1/37211 |
| 2018/0304078 A1* | 10/2018 | Crawford | A61N 1/3758 |
| 2019/0001139 A1* | 1/2019 | Mishra | A61N 1/36146 |
| 2019/0374776 A1* | 12/2019 | Mishra | A61N 1/36125 |

OTHER PUBLICATIONS

Extended European Search Report, Application No. 19181968.9, dated Oct. 23, 2019.

* cited by examiner

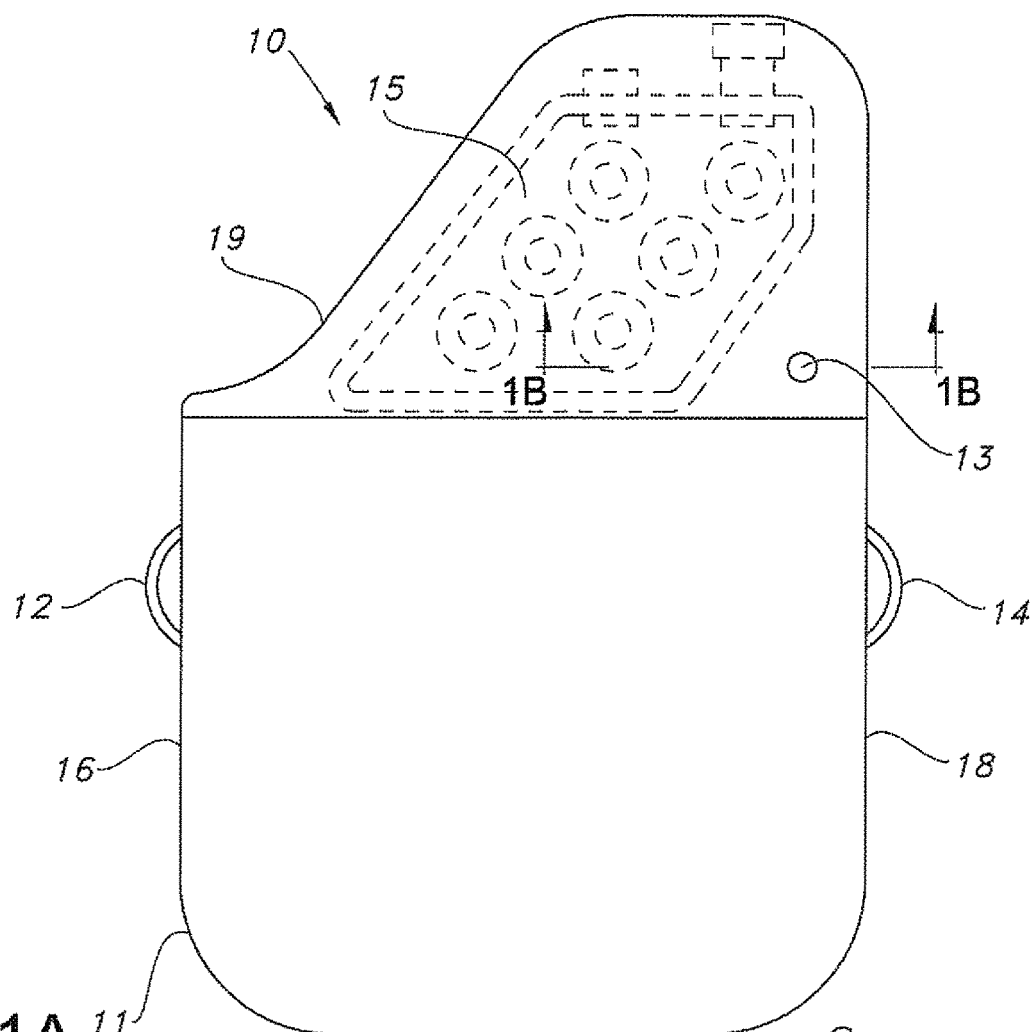
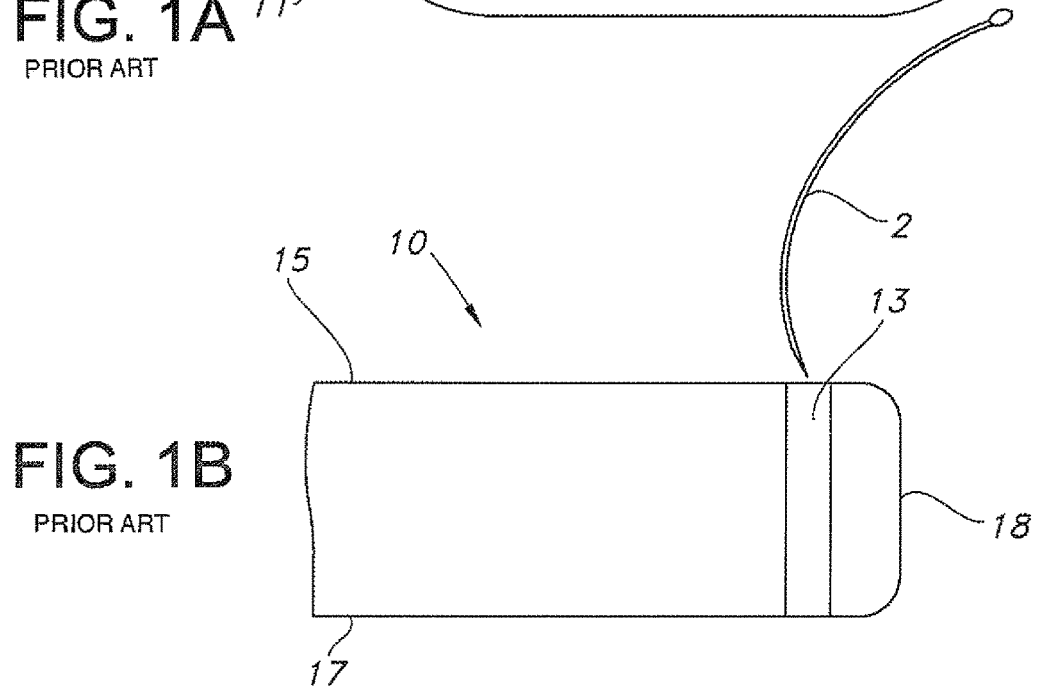
FIG. 1A
PRIOR ART
FIG. 1B
PRIOR ART

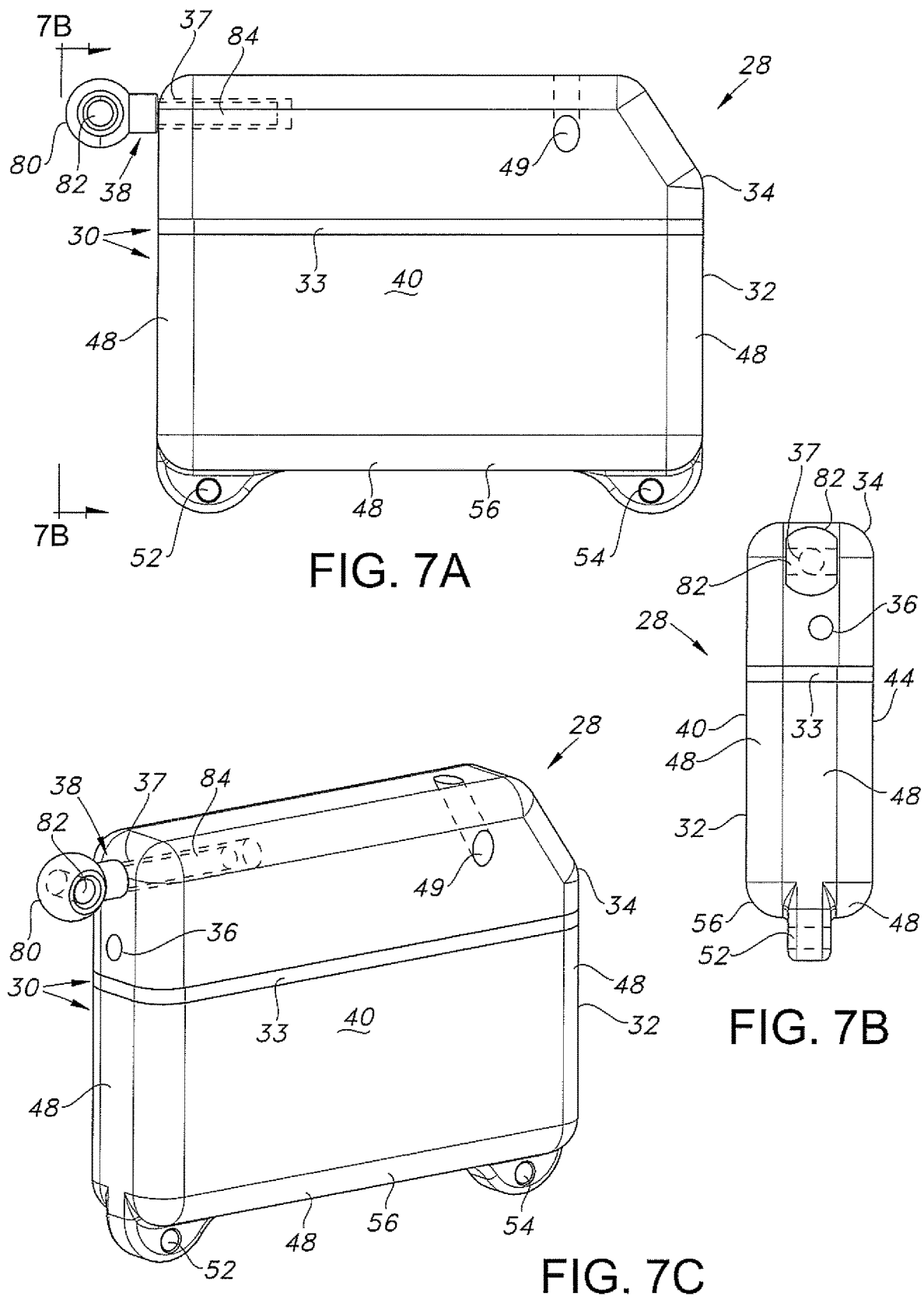

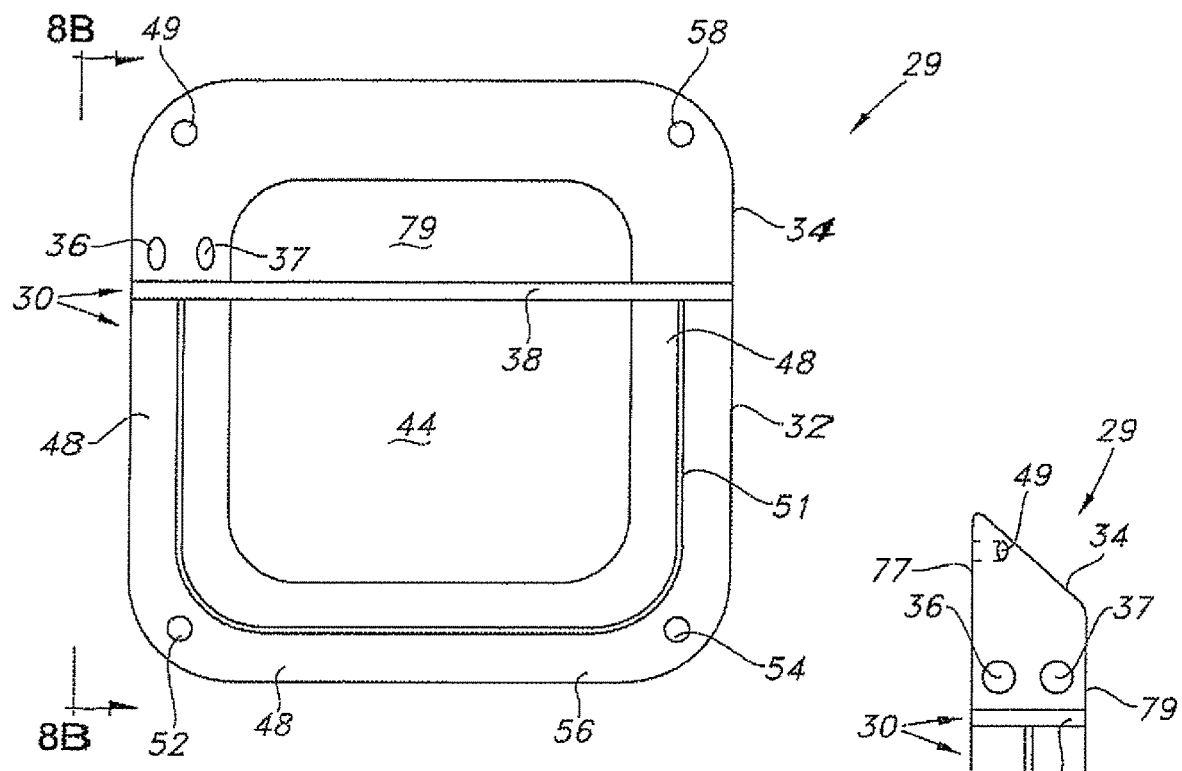
FIG. 8A
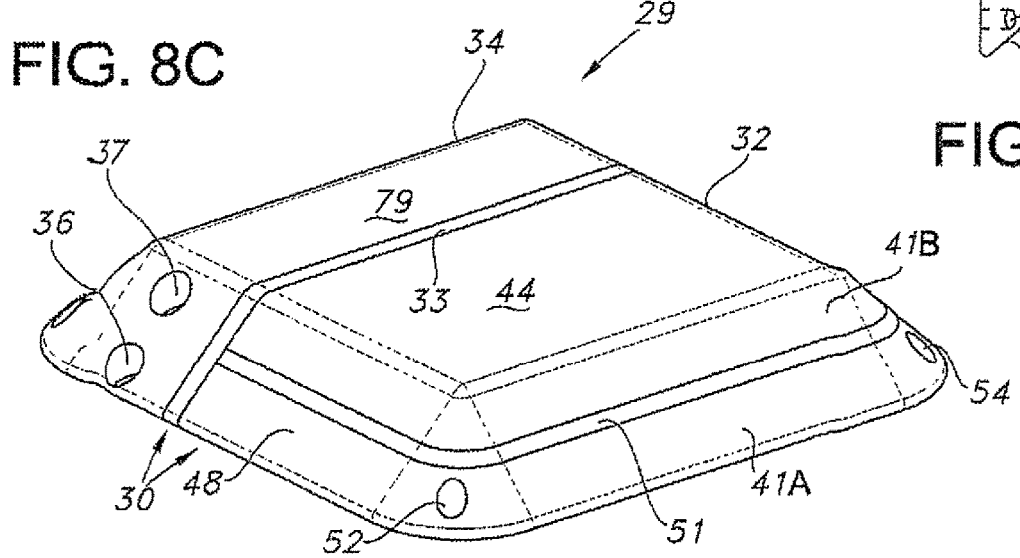
FIG. 8C
FIG. 8B

IMPLANTABLE PULSE GENERATOR WITH MULTIPLE SUTURE PORTS

CROSS-REFERENCE TO RELATED PATENT APPLICATIONS

This application claims the benefit of U.S. Provisional Patent Application No. 62/688,415, filed Jun. 22, 2018, the disclosure of which is incorporated herein by reference. The above benefit claim is being made in an Application Data Sheet submitted herewith in accordance with 37 C.F.R. 1.76 (b)(5) and 37 C.F.R. 1.78.

BACKGROUND

Technical Field

The present disclosure relates to implantable medical devices that generate and disperse electrical energy into human or animal body tissues. More particularly, it relates to implantable medical devices that are configured to facilitate surgical implantation procedures, and to resist migration subsequent to implantation.

Description of Related Art

An implantable pulse generator (IPG) is a device that is capable of generating pulses of electrical energy that are dispersed into human or animal body tissue for a medical purpose. Examples of IPGs are cardiac pacemakers, cardioverter-defibrillators, deep brain stimulators, gastric electrical stimulators, spinal cord stimulators, dorsal root ganglion stimulators, and the like. Such devices have a rounded, square, or other curvilinear shape on the order of 5-50 square centimeters and a thickness of about 0.25-1.5 centimeters. A typical IPG includes a housing formed of a biocompatible material such as titanium, a battery, and a microprocessor in communication with electronic circuitry (capacitors, inductors, resistors, etc.) that is operable to produce electrical pulses for conduction into the body when needed. The device is hermetically sealed to isolate its internal contents from tissue and fluid of the body within which the device is implanted. An IPG further includes one or more electrical terminals or leads for conducting electrical pulses into the body tissue to perform the intended medical treatment.

For any particular IPG, it is necessary that the device be immobilized in the body tissue within which it is implanted. Otherwise, over an extended period of time, the device may migrate within the body tissue to a different location or position. The problem of an implanted IPG moving laterally, rotating, or inverting is even more pronounced for smaller IPGs. Such unintended migration may render the device ineffective in performing its intended function, ineffective for remote induction recharging, and/or may cause other medical complications in the patient.

In order to immobilize an IPG in the body tissue of a patient, the IPG is provided with fastening features that are engageable to body tissue with sutures. When a surgeon implants an IPG into the body of a patient, the surgeon may fasten the IPG to body tissue by looping sutures through the fastening features and through the local body tissue, thereby immobilizing the IPG with respect to location and angular orientation in the body.

FIG. 1A depicts an IPG with conventional fastening features. The IPG 10 is comprised of a titanium casing 11, and suture loops 12 and 14 welded to opposed lateral walls 16 and 18 of the casing 11. Although the loops 12 and 14 may be effective in performing the function of immobilizing the IPG in body tissue, they have certain undesirable aspects. In order to join a suture loop 12/14 to the casing 11, the loop must first be formed from a piece of material that is joinable to the casing 11. In instances where a casing of titanium is used, the wire may also be of titanium. The wire piece must be cut and formed into an arcuate shape. The shaped wire piece must then be welded to the casing at its end points. The wire is on the order of one millimeter in diameter. Hence, the welds must be on a very small dimensional scale, but also of high precision.

In manufacturing IPGs, such a welding task is difficult for a human to perform on a consistent basis. Thus, robotic welding is often used to form the welds. Providing robotic welding machines in a manufacturing plant adds a significant capital equipment cost, and the programming, oversight, and maintenance of the robots add significant operating costs. Moreover, even with the relatively precise operation of robots, adjustment of them is often needed, which is disruptive to manufacturing IPGs in high volumes. During welding, the presence of any dust or other contaminants may weaken a welded joint. Subsequent to welding, an additional finishing step is needed to smooth the surface of the welds.

The welds must also be inspected in order to comply with regulations of the Food and Drug Administration (FDA). The inspection steps also require significant capital investment for the optical, imaging, and metrology (science of weight and measure) equipment. Programming, operation, and maintenance of the equipment and documentation and archiving of the resulting data add to operational costs. Strict manufacturing process validations and manufacturing process monitoring are also required by the FDA.

In addition to the capital and operating costs, the steps of welding and inspection add to the overall cycle time of the IPG manufacturing process, thus reducing the throughput of the manufacturing operation. Other problems related to preparation of an IPG for implantation, the implantation procedure, and the ongoing use of the device in a patient may also occur. The welds of the wire loops to the titanium enclosure are prone to trapping pathogens and causing failure of IPG sterilization procedures. Further, the welded wire loops may cause tissue erosion or irritation in a patient due to their relatively sharp edges on the perimeter of the IPG housing. Finally, the welded wire loops and/or the welds may break while the IPG is implanted and in use. This can enable migration of the device in the patient, rendering its function useless.

An IPG of FIG. 1A may include a suture port 13 that extends through the casing 11 or header 19. Referring to FIG. 1B, the suture port extends between a front wall 15 and a back wall 17 of the device 10. Such a suture port 13 is also problematic because it is difficult for a surgeon to pass a surgical needle 2 carrying a suture (not shown) through the relatively long passageway of the suture port 13. A needle of relatively large radius may be required, which is incompatible with the need for the suturing to be of limited depth into the body tissue. Additionally, the region of the device 10 that is proximate to the suture port 13 must be of solid casing or header material. The suture port cannot pass through the interior cavity of the device 10 that houses internal components. Thus, any suture ports having the structure of suture port 13 will result in a reduced volume for internal device components, which is undesirable.

In view of the disadvantages of conventional fastening features that are presently used in IPGs, there is a need for improved IPG fastening features that simplify the IPG manufacturing process, reduce manufacturing costs, and decrease manufacturing cycle time. There is also a need to improve patient outcomes in implanting IPGs. In particular, there is a need for more reliable anchoring of an IPG to the tissue of a patient in order to prevent migration of the IPG within the patient.

SUMMARY

In accordance with the present disclosure, the problem of immobilizing an implantable pulse generator (IPG) in the body of a patient is solved by forming the fastening features into the housing of the pulse generator in a manner that facilitates implantation, and maximizes internal volumes for housing components. In other words, the fastening features are integrally formed within the housing of the IPG. A fastening feature may be an opening formed in the housing of the IPG. The length, diameter, and angular direction of the opening, and the shape of the pulse generator may be selected so as to facilitate implantation of the generator by a surgeon, and to maximize the hermetically sealed internal volume that is available to contain generator components. An IPG made in such a manner provides for improved anchorage to a patient, and a simplified manufacturing process that can be done at a reduced cost and cycle time. The conventional steps of welding, wire loop bending, cutting, clearing, weld inspection, and weld data management are eliminated.

More particularly, in accordance with the present disclosure, a device that is implantable in body tissue of a human or animal is provided. The device is comprised of a header comprising at least one terminal adapted for removable connection to a lead and an open-ended case closed by a plate to form a housing. The housing is comprised of a surrounding edge wall joined to a first side wall and a second side wall opposed to the first side wall. The edge wall may be formed with a central flat region bounded by curved outer regions and that are contiguous with the respective first and second side walls. Alternatively, the radius of curvature of the curved outer regions may be sufficiently large so that they meet to form a continuously rounded surrounding edge wall. At least a first suture port extends through the edge wall and the second side wall but not the first side wall of the housing. A second suture port may extend through the surrounding edge wall and the second side wall but not the first side wall at a lower edge region of the housing. Additionally, a third suture port may extend through the surrounding edge wall and the second side wall but not the first side wall of the housing. Alternatively, a third suture port may extend through the header. In one aspect of the present disclosure, the three suture ports are formed proximate to a perimeter edge of the device so as to define a triangular attachment configuration. Advantageously, when the device is sutured to the tissue of a patient, the triangular attachment configuration provides a more stable attachment to the patient.

The device may include a fourth suture port. In certain embodiments, the first side wall and the second side wall of the housing may be substantially rectangular in shape. The first and second rectangular-shaped side walls of the housing define first and second corner regions of the device. The header may include third and fourth corner regions of the device. In such embodiments, the first, second, third, and fourth suture ports may extend through the housing proximate to the respective first, second, third, and fourth corner regions. The first, second, third, and fourth suture ports may be aligned substantially perpendicular to the second side wall. In an alternative embodiment, an upper edge region of the device may be comprised of an upwardly extending protuberance with the fourth suture port formed in that protuberance. In another alternative embodiment, the device may be further comprised of a second terminal formed in the header, and a terminal plug with a proximal end disposed in the second terminal. A distal end of the terminal plug may be formed with the fourth suture port extending therethrough.

In another alternative embodiment, the device may be further comprised of a first lateral edge region including a first laterally extending protuberance and a second lateral edge region opposed to the first lateral edge region and including a second laterally extending protuberance. In such an embodiment, the fourth suture port may be formed in the first laterally extending protuberance and a fifth suture port may be formed in the second laterally extending protuberance.

In another alternative embodiment of the present disclosure, the first side wall and the second side wall may be substantially parallel to each other. The first side wall of the device defines an exterior facing surface of the device, and the second side wall of the device defines an interior facing surface of the device. The exterior facing surface of the device is smaller than the interior facing surface of the device. This causes the surrounding edge wall of the device to be sloped towards the exterior facing surface. Patients with an implanted device sometimes manipulate their device under the skin and can cause it to move or even flip front-to-back in orientation. This is referred to as "twiddlers syndrome", and can cause damage to the device system or injury to the patient. The inward sloping surrounding edge wall of the device reduces the patient's ability to externally manipulate the device and impart forces on the device that would cause it to translate or rotate from its intended position.

In fabrication of the device, after electronic components of the device have been placed in a cavity of the case, electrical conductors are passed through orifices in the plate and hermetically sealed to the orifices and the plate. The plate is joined and hermetically sealed to the case by a suitable method such as laser welding, to form a sealed cavity, which protects interior components from the body's environment (warm, moist, conductive, and/or corrosive) and protects the body from interior components that may not be biocompatible or sterile. The header is then molded in place to enclose any electrical conductors extending through the case plate, and to form the terminal(s) and any additional suture ports.

The suture ports are located such that they pass from the second side wall to the surrounding edge wall, and are not in communication with the first side wall of the housing. Thus, the suture ports do not intersect with the hermetically sealed cavity of the case, and the protection of the components therein is ensured.

The implantable device may be provided as an implantable pulse generator, which may be operable as, e.g., a spinal cord stimulator, cardiac pacemaker, cardioverter-defibrillator, deep brain stimulator, gastric electrical stimulator, or dorsal root ganglion stimulator.

BRIEF DESCRIPTION OF THE DRAWINGS

The present disclosure will be provided with reference to the following drawings, in which like numerals refer to like elements, and in which:

FIG. 1A is a front elevation view of a conventional implantable medical device including welded suture loops for securing the device to body tissue;

FIG. 1B is a cross-sectional view of a portion of the device of FIG. 1A, taken along line 1B-1B of FIG. 1A;

FIGS. 7A-7C are front, side, and upper left perspective views of a fourth embodiment of an implantable device of the present disclosure; and FIGS. 8A-8C are front, side, and lower left perspective views of a fifth embodiment of an implantable device of the present disclosure.

Figures 2A, 2B:
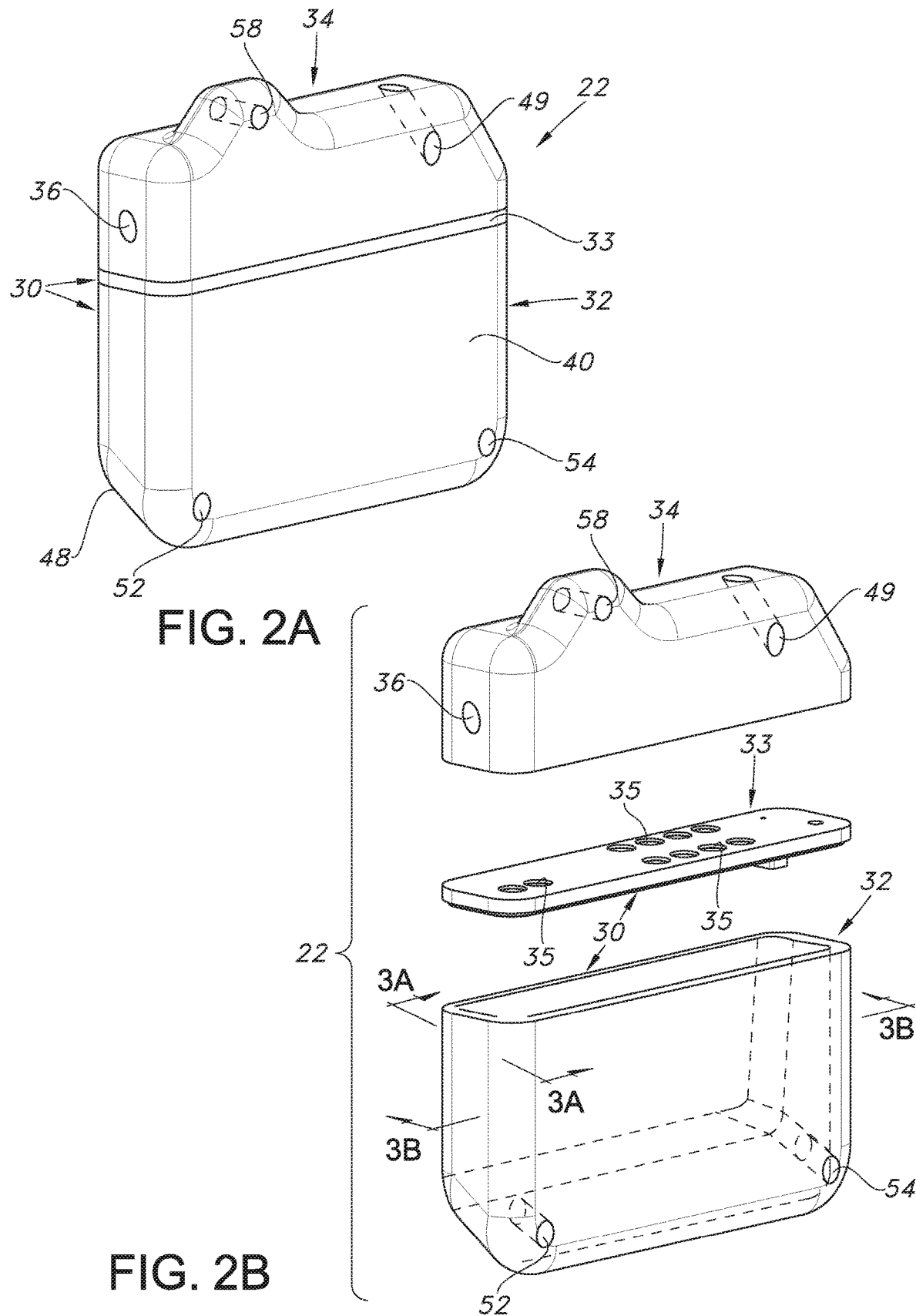
FIG. 2A is perspective view of an exemplary implantable medical device of the present disclosure.
FIG. 2B is an exploded view of the device of FIG. 2A.
Figure 3A:
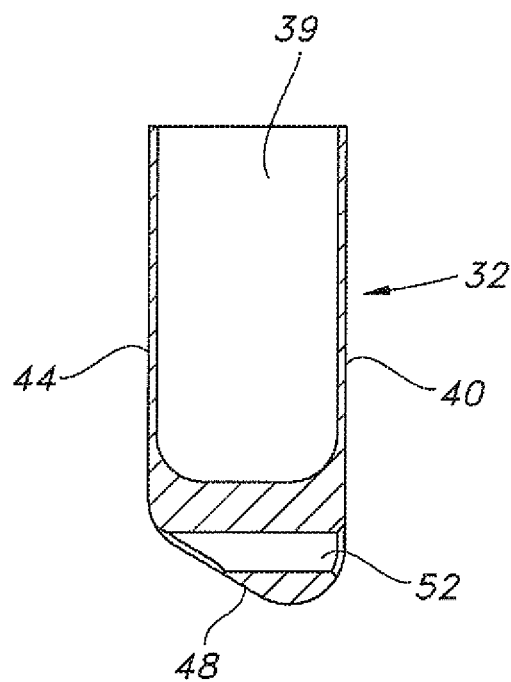
FIG. 3A is an end cross-sectional view of the case of the device of FIG. 2B, taken along line 3A-3A of FIG. 2B.
Figure 3B:
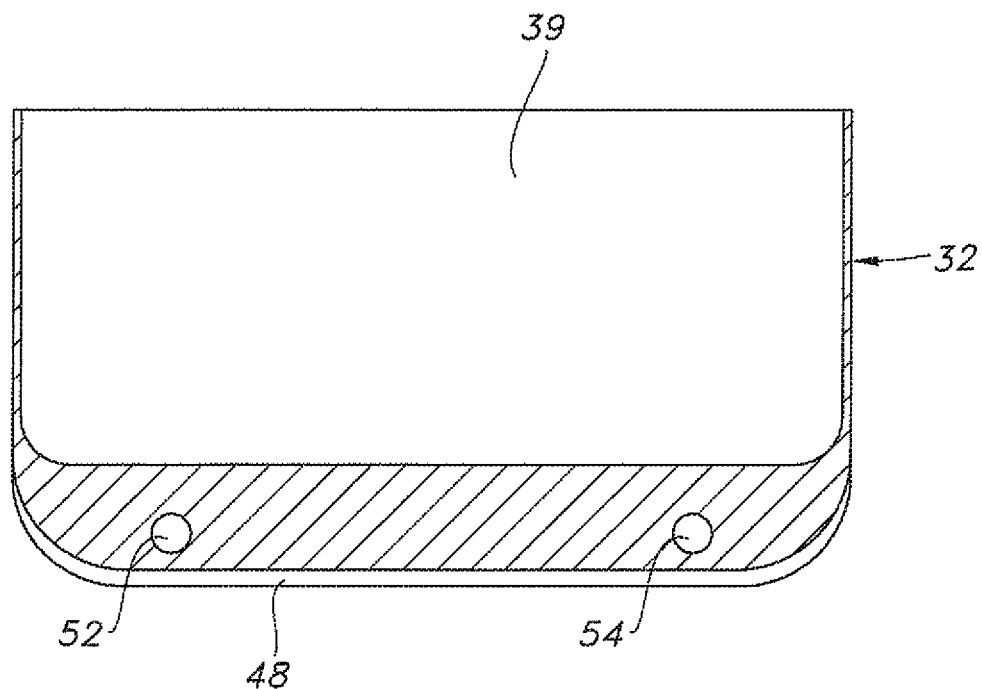
FIG. 3B is a side cross-sectional view of the case of the device of FIG. 2B, taken along line 3B-3B of FIG. 2B.
Figure 4A:
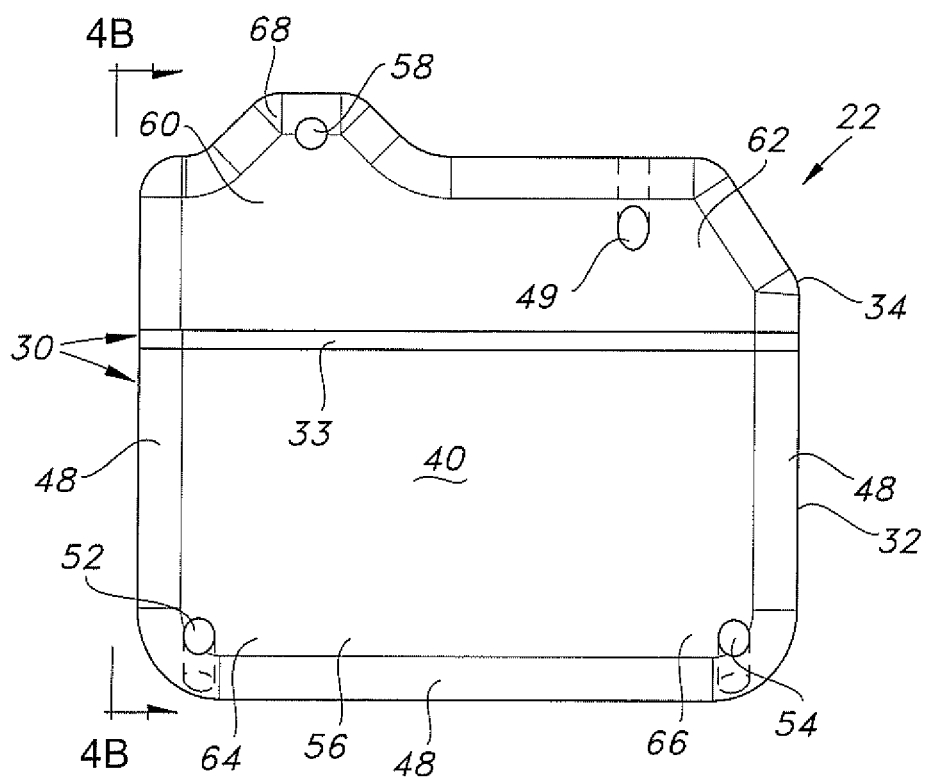
FIGS. 4A-4D are front, side, rear, and upper right perspective views of a first embodiment of an implantable device of the present disclosure, also shown in FIGS. 2A and 2B.
Figure 4B:
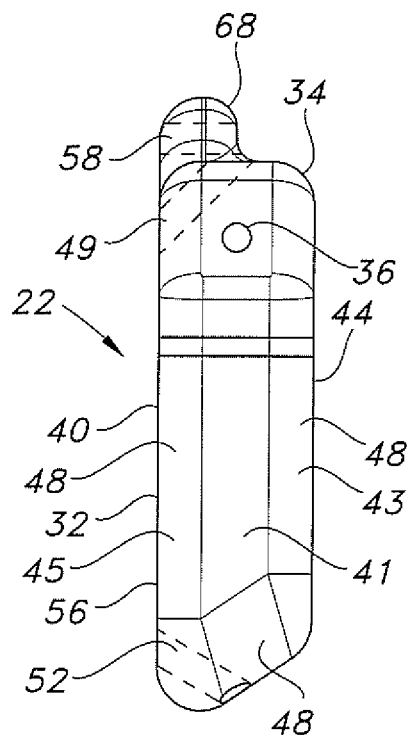
Figure 4C:
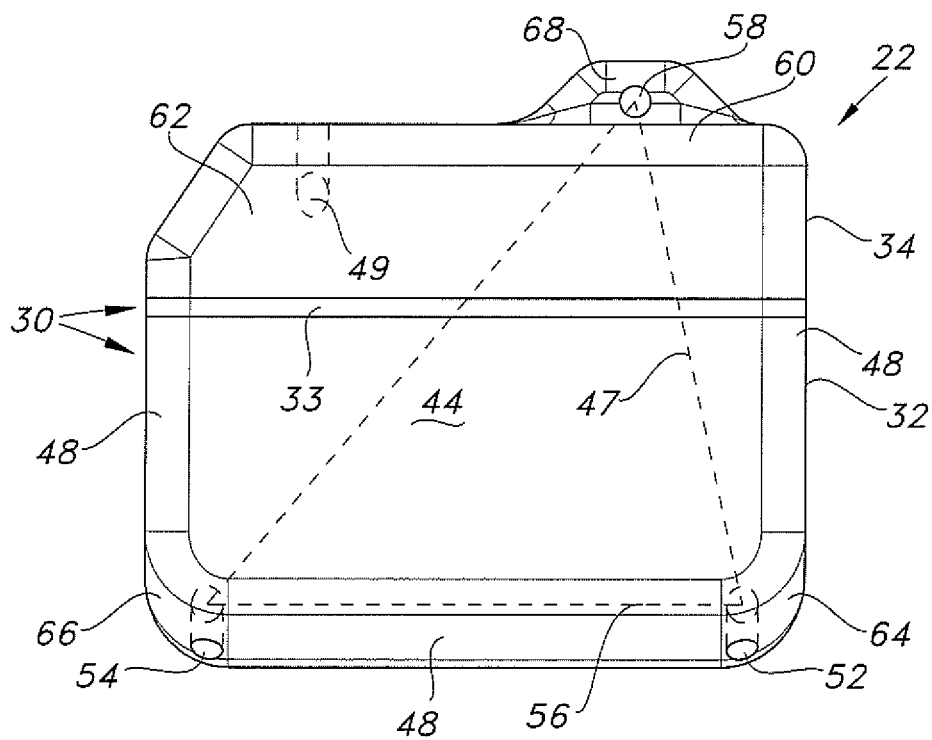
Figure 4D:
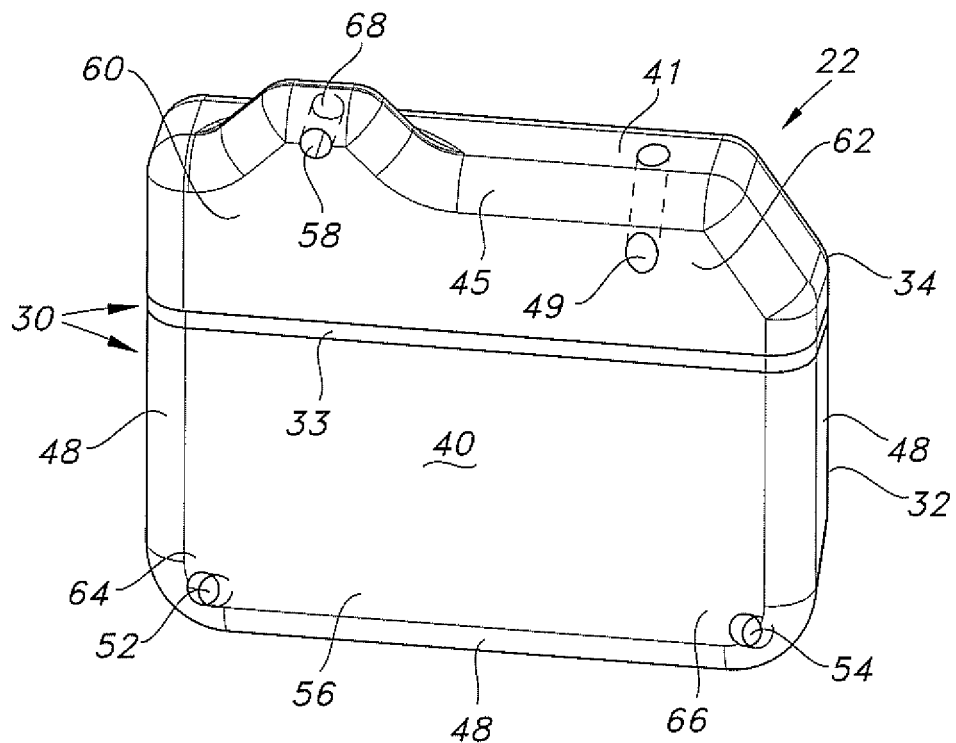
Figure 5A:
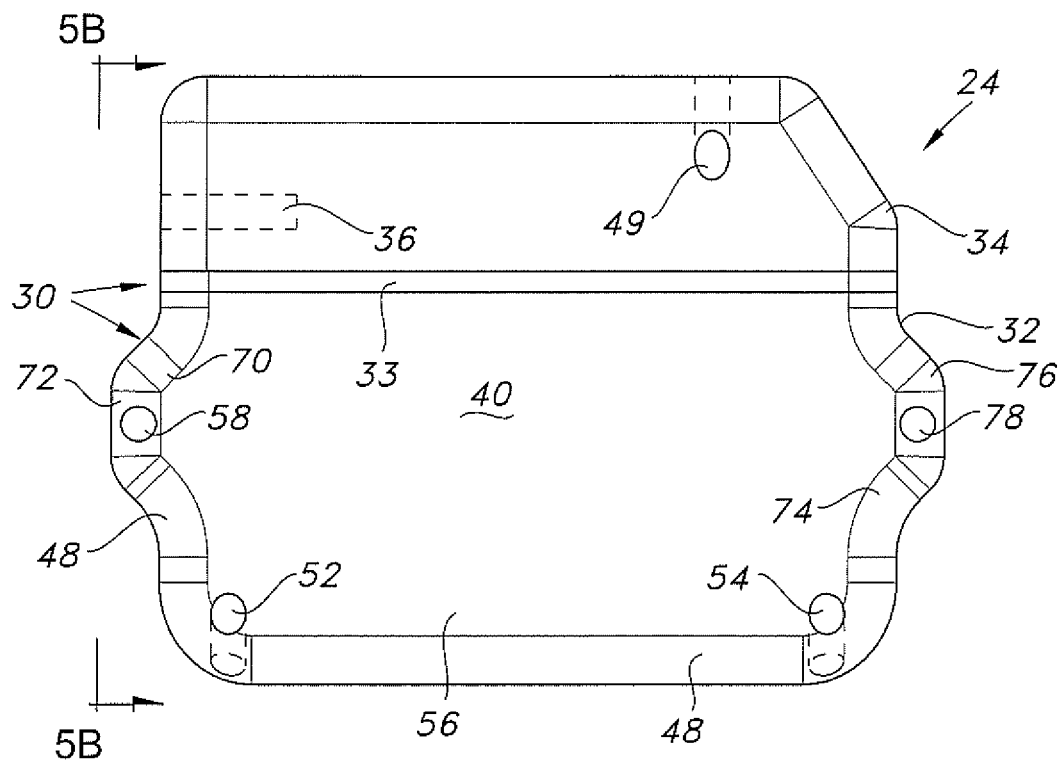
FIGS. 5A-5D are front, side, rear, and upper right perspective views of a second embodiment of an implantable device of the present disclosure.
Figure 5B:
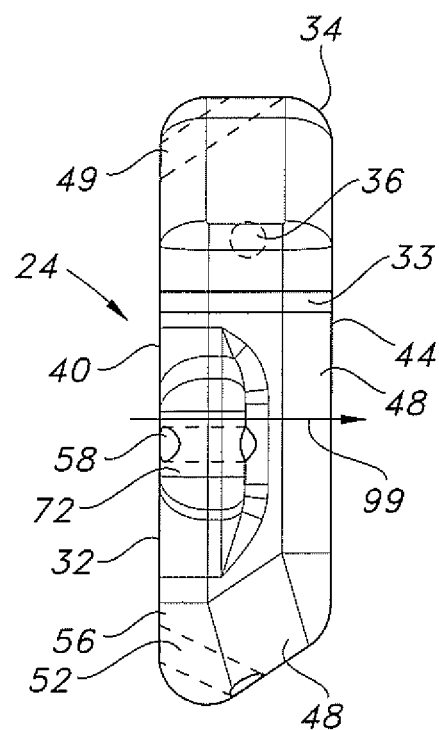
Figure 5C:
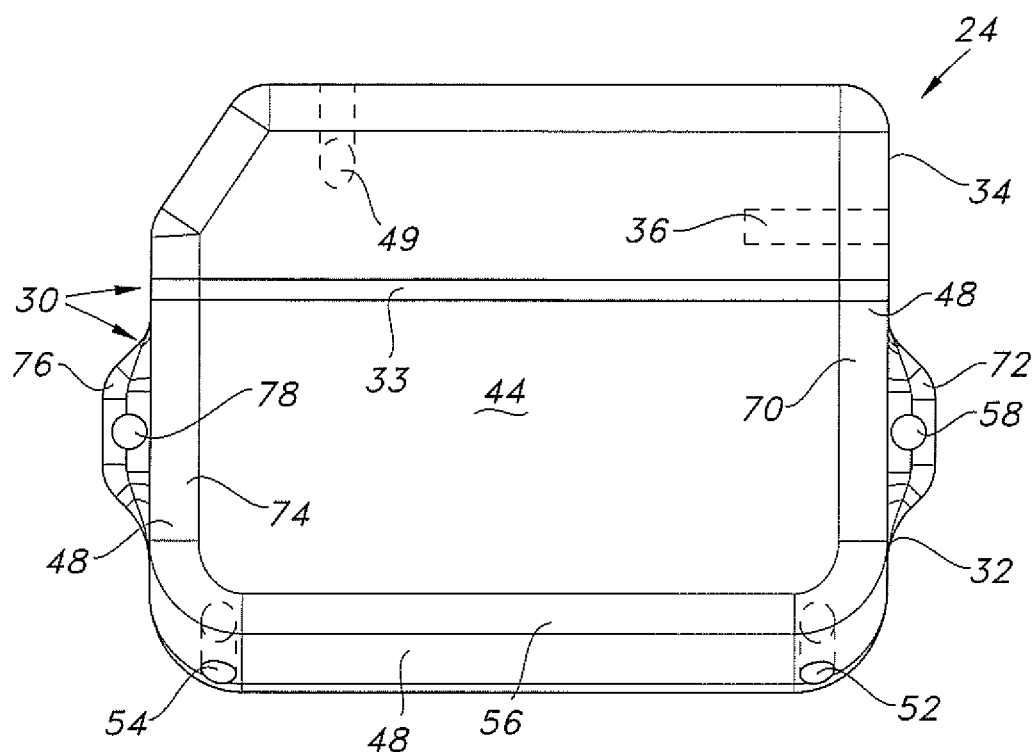
Figure 5D:
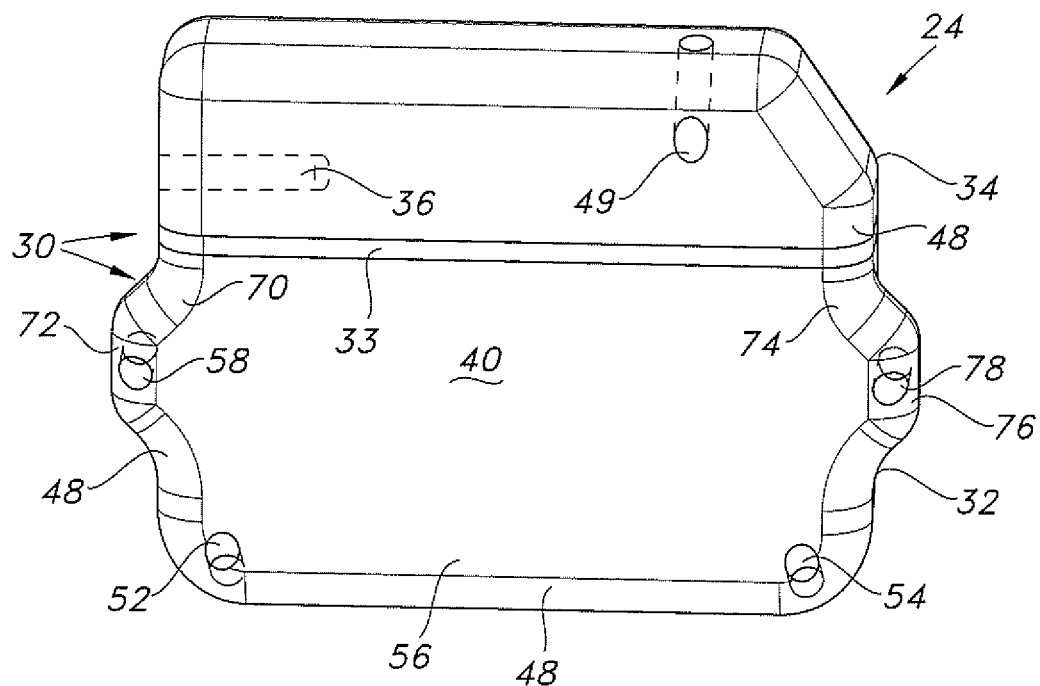
Figure 6A:
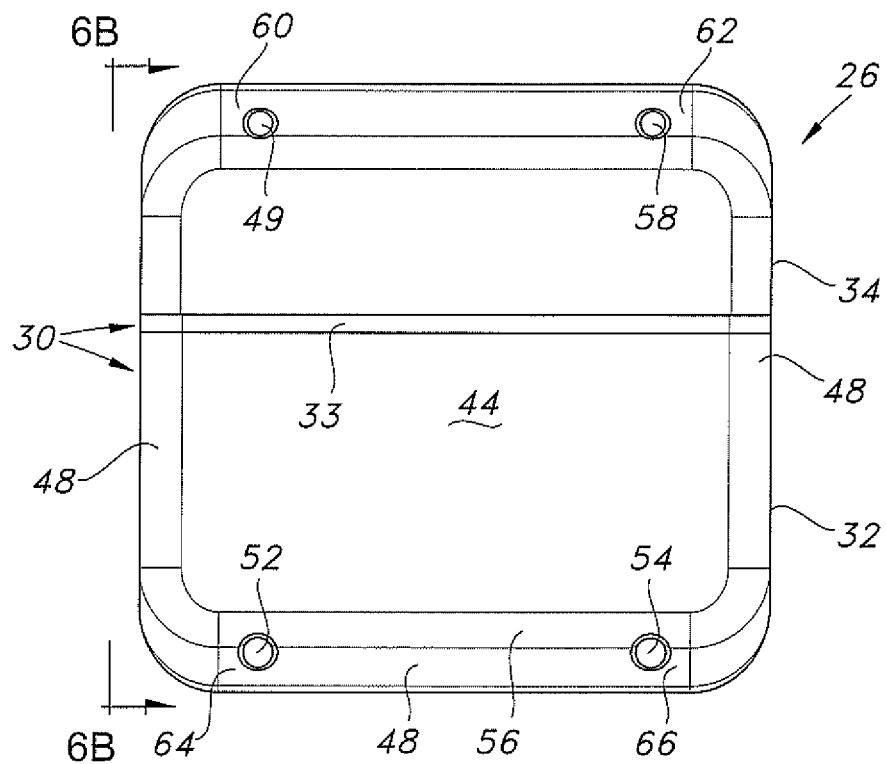
FIGS. 6A-6D are front, side, rear, and upper right perspective views of a third embodiment of an implantable device of the present disclosure.
Figure 6B:
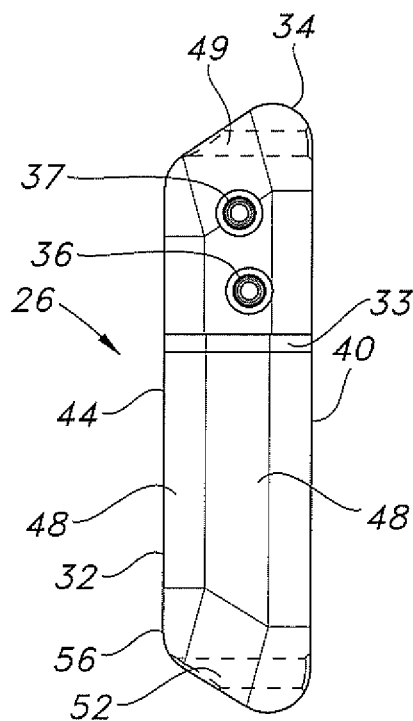
Figure 6C:
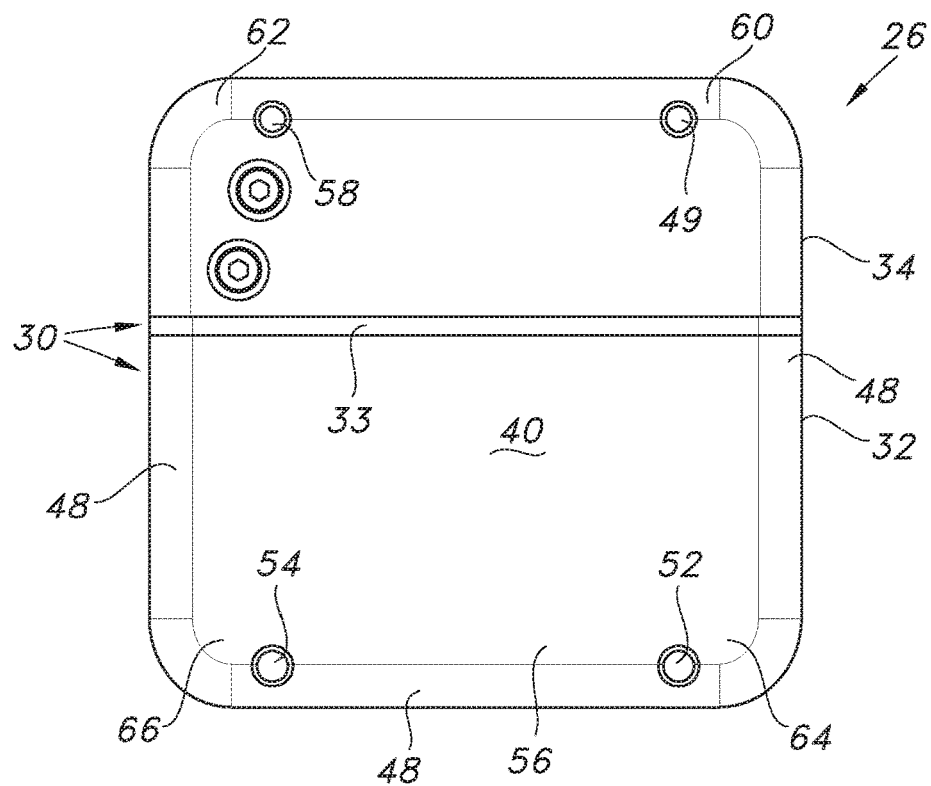
Figure 6D:
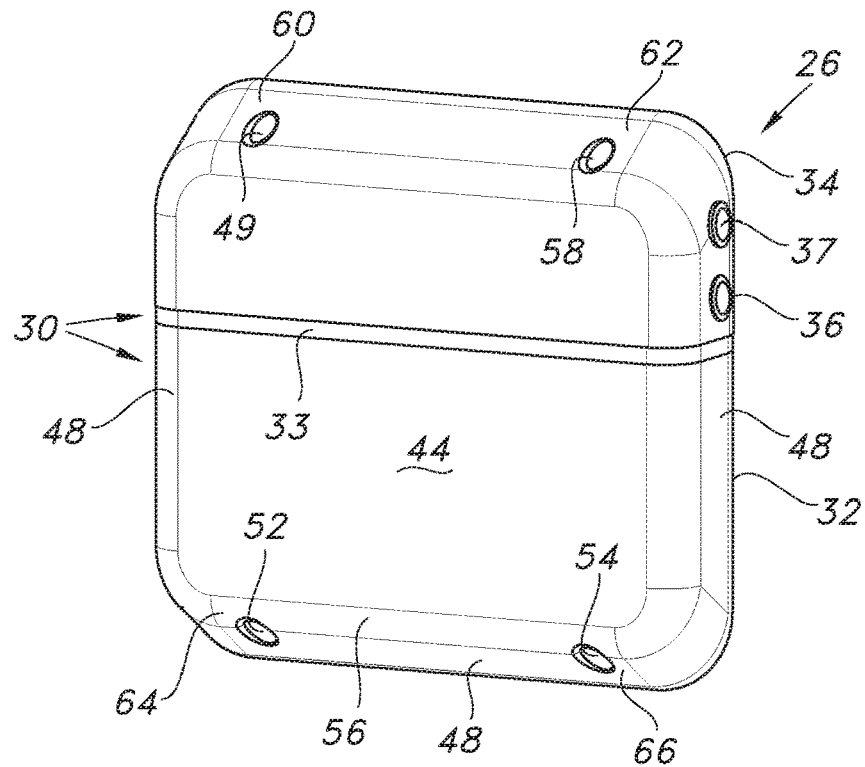

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. The drawings are to be considered exemplary, and are for purposes of illustration only. The dimensions, positions, order, relative sizes, device shapes, and suture hole shapes reflected in the drawings provided herewith may vary.

In the following disclosure, the present invention is described in the context of its use as an implantable pulse generator used for medical purposes in a human or animal. However, it is not to be construed as being limited only to use in generating electrical pulses for therapeutic purposes. The invention is adaptable to any use in which it is desirable to implant and secure a compact device in human or animal body tissue. Additionally, the description may identify certain components with the adjectives "front," "rear," "top," "upper," "bottom," "lower," "left," "right," etc. These adjectives are provided in the context of the orientation of the drawings, which is arbitrary. The description is not to be construed as limiting the device to use in a particular spatial orientation. The device may be implanted and used in orientations other than those shown and described herein.

It is also to be understood that any connection references used herein (e.g., attached, coupled, connected, and joined) are to be construed broadly and may include intermediate members between a collection of elements and relative movement between elements unless otherwise indicated. As such, connection references do not necessarily imply that two elements are directly connected and in fixed relation to each other.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the inventive scope of the present disclosure.

FIGS. 2A, 2B, and 4A-4D depict an exemplary embodiment of a device 22 of the present disclosure. FIGS. 5A-5D through 8A-8C depict four additional embodiments 24, 26, 28, and 29 of an implantable device of the present disclosure. These embodiments share certain features in common, which will first be described with reference to each group of drawings. Subsequently, the specific features unique to a particular embodiment will be described with reference to an individual group of drawings.

Referring to FIGS. 2A-2B, 3A-3B, and 4A-4D through 8A-8C, an implantable device 22, 24, 26, 28, or 29 is comprised of a header 34 comprising at least one terminal 36 adapted for removable connection to a lead (not shown) and an open-ended case 32 closed by a plate 33. Referring in particular to FIG. 2B, and also to FIGS. 3A and 3B, the case 32 is made of a suitable biocompatible material, such as titanium. The case 32 has an internal cavity 39 that is machined or otherwise formed therein, which contains the device electronics (not shown) and power source, such as a battery (not shown).

Referring again to FIGS. 2A and 2B, a housing 30 of the device 22 is comprised of the case 32 and a case plate 33. In fabrication of the implantable device 22, 24, 26, 28, or 29, after the electronic components (not shown) of the device have been placed in the case 32, electrical conductors (not shown) are passed through various orifices 35 in the plate 33 and hermetically sealed to the orifices 35 and plate 33. Any unoccupied orifices 35 are also hermetically sealed. The plate 33 is joined and hermetically sealed to the case 32 by a suitable method such as laser welding. The header 34 is then molded in place to enclose any electrical conductors extending through the case plate 33, and to form the electrical terminal 36.

The header 34 is made of a suitable biocompatible material, such as epoxy, and may be molded in place to enclose any electrical conductors extending through the case plate 33. The header 34 further includes electrical terminal 36 (FIGS. 5A, 5B, 5C, 5D, 6B, 6D, 7B, 7C, and 8A-8C). When the device 22, 24, 26, 28 and 29 is implanted in a patient, an electrical conductor such as an electrical lead (not shown) may be plugged into the electrical terminal 36 for the purpose of conducting electrical signals or pulses to body tissue that is distant from the device 22, 24, 26, 28 and 29. The device 22, 24, 26, 28 and 29 may have multiple electrical terminals 36/37. In circumstances where one of the electrical terminals, e.g., terminal 37, is not connected to an electrical lead, a terminal plug 38 (FIGS. 7A-7C) may be disposed in the electrical terminal 37.

Referring again to FIGS. 2A-2D through 8A-8C, the housing 30 (comprising case 32 closed by plate or lid 33) of device 22, 24, 26, 28 and 29 is comprised of a first side wall 44, a second side wall 40, and a surrounding edge wall 48 joined to the first side wall 44 and to the second side wall 40. The second side wall 40 is opposed to the first side wall 44. The side walls 40 and 44 may be parallel to each other. In the device 22 shown in FIG. 4B, the surrounding edge wall 48 may be formed with a central flat region 41 bounded by curved outer regions 43 and 45 that are contiguous with respective side walls 40 and 44. In other embodiments (not shown), the radius of curvature of the curved outer regions 43 and 45 may be sufficiently large so that they meet to form a convex edge wall, i.e., a continuous outwardly rounded surrounding edge wall 48. A first suture port 52 extends through the housing 30. A second suture port 54 may also extend through the housing 30. The first and second suture ports 52 and 54 extend through the surrounding edge wall 48 and the second side wall 40 but not the first side wall 44 of the housing 30. The first and second suture ports 52 and 54 may be located at a lower edge region 56 of the housing 30.

Referring in particular to FIGS. 5A-5D, a third suture port 78 may extend through the surrounding edge wall 48 and the second side wall 40 but not the first side wall 44 of the housing 30. Alternatively, a third suture port 49 in lieu of suture port 78 may extend through the header 34 as shown for devices 22, 24, 26, 28, and 29 of FIGS. 4A-4D through 8A-8D. Advantageously, the provision of three suture ports (52, 54 and 78 or 52, 54 and 49) distributed over the device in a triangular pattern or configuration and located proximate to the perimeter edge of the second side wall 40 provides more secure anchoring of the device in a patient, thereby preventing any linear and rotational migration. One exemplary triangular pattern 47, which forms a triangular attachment base of the device, is shown in FIG. 40.

The devices 22, 24, 26, 28 and 29 may include a fourth suture port. In the devices 22, 24, 26, 28 and 29 of respective FIGS. 4A-4D, 5A-5D, 6A-6D, 7A-7C and 8A-8C, the first side wall 44 and the second side wall 40 of the housing 30 may be substantially rectangular in shape. The term "substantially rectangular" is considered to include generally rectangular shapes with radiused or beveled corners, and edge protuberances. The first and second rectangular-shaped side walls 44 and 40 define first and second corner regions 64 and 66 of the housing 30. The header may include third and fourth corner regions 60 and 62 of the device. Referring to devices 22 and 26 of FIGS. 4A-4D and FIGS. 6A-6D, respectively, the first, second, third, and fourth suture ports 52, 54, 58 and 49 may extend through the first, second, third, and fourth corner regions 64, 66, 60, and 62 of the device, respectively. Referring to device 26 of FIGS. 6A-6D, the first, second, third, and fourth suture ports 52, 54, 58 and 49 may be aligned substantially perpendicular to the second side wall 40. Referring to device 22 of FIGS. 4A-4D, the upper edge region of the header 34 may be comprised of an upwardly extending protuberance 68, with the fourth suture port 58 formed in the upwardly extending protuberance 68.

Referring to the alternative device 24 of FIGS. 5A-5D, the housing 30 may be further comprised of a first lateral edge region 70 including a first laterally extending protuberance 72 and a second lateral edge region 74 opposed to the first lateral edge region 70 and including a second laterally extending protuberance 76. In such an embodiment, the fourth suture port 58 may be formed in the first laterally extending protuberance 72 and a fifth suture port 78 of device 24 may be formed in the second laterally extending protuberance 76.

The suture ports formed in the housing 30 of the device extend from the second side wall 40 to the edge wall 48, and do not extend to the first side wall 44. For example, in the device 22 of FIGS. 4A-4D, the suture ports 52 and 54 extend from the second side wall 40 to the edge wall 48. The suture ports 52 and 54 of the device 24 of FIGS. 5A-5D are configured in a similar manner. Additionally, the third suture port 49 that is formed in the header 34 of the devices 22 and 24 is configured in a similar manner. By forming the ports in this manner, the ports are canted at an outward angle with respect to the first side wall 44. (In other words, the central axes of the ports 49, 52, and 54 diverge away from each other with respect to a central axis through the device 24 in the direction of arrow 99 in FIG. 58.) Advantageously, when placing the device in the tissue of the patient with the first side wall 44 facing inwardly with respect to the patient, the canted angle of the ports 49, 52, and 54 facilitates the passage of sutures through the ports 49, 52, and 54 by the surgeon.

Referring to FIGS. 7A-7C, the device 28 shown therein is similar to the devices 22, 24, and 26. Device 28 includes a first side wall 44, a second side wall 40, an edge wall 48, and suture ports 52 and 54. Device 28 may also include suture port 49 in the header 34. Additionally, device 28 is further comprised of an electrical terminal 36 formed in the edge wall 48 of the housing 30. As described previously, when the device 28 is implanted in a patient, an electrical conductor such as an electrical lead (not shown) may be plugged into one of the electrical terminals, e.g., terminal 36, for the purpose of conducting electrical signals or pulses to body tissue that is distant from the device 28. In circumstances where the electrical terminal 37 is not connected to an electrical lead, a terminal plug 38 may be disposed in the electrical terminal 37. The terminal plug 38 is comprised of a distal end 80 with a first suture port 82 extending therethrough, and a proximal end 84 disposed in the electrical terminal 37.

Referring to the alternative device 29 of FIGS. 8A-8C, the device 29 is comprised of case 32, case plate 33, and header 34. The device 29 may have the shape of a truncated square pyramid, appearing as a trapezoidal shape in the side view of FIG. BB. The first side wall 44 and the second side wall 40 are substantially parallel. When the device 29 is implanted in a patient (not shown), the first side wall 44 is an exterior facing surface, i.e. it faces outwardly with respect to the body of the patient and the second side wall 40 is an interior facing surface, facing inwardly with respect to the body of the patient. The exterior facing surface/side wall 44 of the casing 32 and the exterior facing surface/side wall 79 of the header 34 are made smaller in surface area than the interior facing surface/side wall 40 and the interior facing surface/side wall 77 of the header of the device 29. This causes the edge walls 48 of the device 29 to be sloped towards the exterior facing surface 44. In certain embodiments, the area of the first side wall may be between 85%-95% of the area of the second side wall, optionally between 75%-85% of the area of the second side wall, and further optionally between 65%-75% of the area of the second side wall. Advantageously, the inward sloping edge walls 48 of the device 29 reduce the ability of a patient to "twiddle" the device, i.e., to externally manipulate the device 29 and impart forces on the device 29 that would cause it to translate or rotate from its intended position.

Referring again to FIGS. 8A-8C, the case 32 of device 29 may be comprised of separate parts that form the interior facing surface 40 or exterior facing surface 44. A sealed cavity (not shown) is formed by the casing 32 to protect interior components from the body's environment (warm, moist, conductive, and/or corrosive) and to protect the body of the patient from interior components that may not be biocompatible or sterile. In order to produce the sealed interior volume, the case 32 and case plate 33 must be joined together with a liquid and gas tight hermetic connection. In the embodiment depicted in FIGS. 8A-8C, the case 32 is comprised of an inner flat portion 41A and an outer flat portion 41B, suitably joined and hermetically sealed to each other, such as by a laser weld 51. The upper opening of the case 32 is joined and hermetically sealed to the case plate 33 as described previously. The suture ports 49, 58, 52, and 54 extend through the surrounding edge wall 48 and the second side wall 40 but not the first side wall 44 of the housing 30.

In attaching an IPG device to a patient, the surgeon must pass a needle with a suture through a suture port of the device at least once, and possibly several times. The suturing needle typically has a substantial radius of curvature so that it will arc into and back out of attachment tissue of the patient. Referring to FIG. 1B, it can be seen that for a prior art device 10, it will be difficult to pass an arcuate suturing needle 2 through the suturing port 13, which traverses the entire thickness of the device 10. In contrast, all of the suture ports of the devices 22, 24, 26, 28, and 29 of FIGS. 2A, 2B, 3A, 3B, 4A-4D, 5A-5D, 6A-6D, 7A-7C and 8A-8C share a common attribute, in that all are configured to facilitate the attachment of the device to a patient. In one aspect, the suture ports are formed in the housing of the device such that they are shorter in length while being of sufficiently large diameter to render it easier to pass a curved suture needle through. They may be made shorter by having the surrounding edge wall 48 angled or beveled with respect to the first and second side walls 44 and 40, and locating the suture ports in a region of reduced thickness. (See FIGS. 6A-6D and 8A-8C.) Additionally, the suture ports that pass through such beveled walls may also be angled with respect to the first and second side walls 44 and 40 of the device. (See FIGS. 4A-4D and 5A-5D.) Such an arrangement may be more optimal for passing a needle through a patient's tissue and through a suture port. Alternatively, the suture ports may be made shorter by locating them in protuberances as described previously. The protuberances may be of reduced thickness relative to the overall thickness of the device. (See FIGS. 5A-5D and 7A-7D.) In general, suture ports of the devices 22, 24, 26, 28, and 29 pass through the second side wall 40 and the surrounding edge wall 48, and not through the first side wall 44.

The case 32, case plate 33, and the header 34 may be made by any process that is capable of forming parts of the required biocompatible material, including but not limited to machining, stamping, molding or casting, or an additive manufacturing process, such as fused deposition modelling (a.k.a. "3D printing"), selective laser sintering, or stereolithography. In instances where the case 32 is made of a metal such as titanium, the suture ports may be formed by using a drill bit or a laser. The case plate 33 may also be made of titanium to facilitate the welding to a case 32 made of titanium. The header 34 is typically made of a clear biocompatible polymer such as an epoxy. The suture ports in the header 34 may be cast in place or formed by drilling. The exterior edges of the suture ports are preferably deburred and/or chamfered, so that no sharp edges are present that might otherwise stress or cut the sutures.

It is therefore apparent that there has been provided, in accordance with the present disclosure, a device that is implantable in body tissue of a human or animal. The foregoing description of technology and the invention is merely exemplary in nature of the subject matter, manufacture, and use of the invention and is not intended to limit the scope, application, or uses of any specific invention claimed in this application or in such other applications as may be filed claiming priority to this application, or patents issuing therefrom.

The description and specific examples, while indicating embodiments of the technology disclosed herein, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

Unless otherwise specified, relational terms used in the present disclosure should be construed to include certain tolerances that those skilled in the art would recognize as providing equivalent functionality. By way of example, the term perpendicular is not necessarily limited to 90.00°, but also to any variation thereof that those skilled in the art would recognize as providing equivalent functionality for the purposes described for the relevant member or element. Terms such as "about" and "substantially" in the context of configuration relate generally to disposition, location, and/or configuration that is either exact or sufficiently close to the location, disposition, or configuration of the relevant element to preserve operability of the element within the invention while not materially modifying the invention. Similarly, unless specifically specified or clear from its context, numerical values should be construed to include certain tolerances that those skilled in the art would recognize as having negligible importance, as such do not materially change the operability of the invention.

Having thus described the basic concept of the invention, it will be apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be expressly stated in the claims.

What is claimed is:

1. A device that is implantable in body tissue of a human or animal, the implantable device comprising:
   a) a header comprising at least one terminal adapted for removable connection to a lead;
   b) a housing connected to the header, the housing comprised of an exterior facing side wall that is parallel to and lesser in area than an interior facing side wall, wherein a surrounding edge wall is joined to and at least in part slopes from the interior facing side wall to the exterior facing side wall, and wherein at least a portion of the surrounding edge wall between the interior facing and exterior facing side walls is flat;
   c) electronic circuitry contained in the housing, wherein the electronic circuitry is electrically connected to the at least one terminal and is configured to produce electrical pulses for conduction into body tissue; and
   d) at least one suture port extending through the sloped surrounding edge wall and the interior facing side wall but not through the exterior facing side wall of the housing,
   e) wherein, for reduced external manipulability, the exterior facing side wall is adapted to face outwardly with respect to the body of the human or animal and the interior facing side wall is adapted to face inwardly with respect to the body of the human or animal.

2. The implantable device of claim 1, further comprising a second suture port extending through the surrounding edge wall and the interior facing side wall but not through the exterior facing side wall of the housing.

3. The implantable device of claim 2, further comprising a third suture port extending through the surrounding edge wall and the interior facing side wall but not through the exterior facing side wall of the housing.

4. The implantable device of claim 2, further comprising a third suture port extending through the header.

5. The implantable device of claim 4, wherein the first, second, and third suture ports are canted at an outward angle with respect to the exterior facing side wall of the housing.

6. The implantable device of claim 4, wherein the first, second, and third suture ports are formed proximate to a perimeter edge of the device and define a triangular attachment configuration for the device.

7. The implantable device of claim 1, wherein at least one of the interior facing and exterior facing side walls is joined to the flat portion of the surrounding edge wall by a curved region.

8. The implantable device of claim 4, further comprising a fourth suture port.

9. The implantable device of claim 8, wherein the exterior facing side wall and the interior facing side wall are substantially rectangular-shaped side walls.

10. The implantable device of claim 9, wherein the exterior facing and interior facing substantially rectangular-shaped side walls define first and second corner regions of the device, and wherein the header defines third and fourth corner regions of the device, and wherein the first, second, third, and fourth suture ports extend through the first, second, third, and fourth corner regions of the device, respectively.

11. The implantable device of claim 10, wherein the first, second, third, and fourth suture ports are aligned substantially perpendicular to the interior facing side wall of the housing.

12. The implantable device of claim 8, wherein an upper edge region of the header is comprised of an upwardly extending protuberance, and the fourth suture port is formed in the upwardly extending protuberance.

13. The implantable device of claim 8, further comprising a second terminal formed in the header, and wherein a proximal end of a terminal plug is disposed in the second terminal with a distal end of the terminal plug having a terminal plug suture port.

14. A device that is implantable in body tissue of a human or animal, the implantable device comprising:
   a) a header comprising at least one terminal adapted for removable connection to a lead, and further comprising a first suture port that extends through the header; and
   b) a housing connected to the header, the housing comprised of:
      i) an exterior facing side wall that is parallel to and lesser in area than an interior facing side wall, wherein a surrounding edge wall is joined to and at least in part slopes from the interior facing side wall to the exterior facing side wall, and wherein at least a portion of the surrounding edge wall between the interior facing and exterior facing side walls is flat; and
      ii) at least a second suture port spaced from a third suture port, wherein the second and third suture ports each extends through the surrounding edge wall and the interior facing side wall but not through the exterior facing side wall of the housing, and wherein the second and third suture ports are canted at an outward angle with respect to the exterior facing side wall of the housing,
   c) wherein, for reduced external manipulability, the exterior facing side wall is adapted to face outwardly with respect to the body of the human or animal and the interior facing side wall is adapted to face inwardly with respect to the body of the human or animal.

15. The implantable device of claim 14, further comprising a fourth suture port extending through the surrounding edge wall and the interior facing side wall but not through the exterior facing side wall of the housing.

16. The implantable device of claim 15, wherein the fourth suture port is canted at an outward angle with respect to the exterior facing side wall of the housing.

17. The implantable device of claim 14, wherein at least one of the interior facing and exterior facing side walls is joined to the flat portion of the surrounding edge wall by a curved region.

18. The implantable device of claim 17, wherein a first area of the exterior facing side wall is from about 85% to about 95% of a second area of the interior facing side wall of the housing.

19. The implantable device of claim 17, wherein a first area of the exterior facing side wall is from about 75% to about 85% of a second area of the interior facing side wall of the housing.

20. The implantable device of claim 17, wherein a first area of the exterior facing side wall is from about 65% to about 75% of a second area of the interior facing side wall of the housing.

21. A device that is implantable in body tissue of a human or animal, the implantable device comprising:
   a) a header comprising at least one terminal adapted for removable connection to a lead, and further comprising a first suture port that extends through the header; and
   b) a housing connected to the header, the housing comprised of:
      i) an exterior facing side wall that is parallel to and lesser in area than an interior facing side wall, wherein a surrounding edge wall is joined to and at least in part slopes from the interior facing side wall to the exterior facing side wall, and wherein a first area of the exterior facing side wall is from about 75% to about 95% of a second area of the interior facing side wall of the housing; and
      ii) at least a second suture port spaced from a third suture port, wherein she second and third suture ports each extends through the surrounding edge wall and the interior facing side wall but not through the exterior facing side wall of the housing, and wherein the second and third suture ports are canted at an outward angle with respect to the exterior facing side wall of the housing,
   c) wherein, for reduced external manipulability, the exterior facing side wall is adapted to face outwardly with respect to the body of the human or animal and the interior facing side wall is adapted to face inwardly with respect to the body of the human or animal.

* * * * *